US012588867B2

(12) United States Patent
Collins et al.

(10) Patent No.: US 12,588,867 B2
(45) Date of Patent: Mar. 31, 2026

(54) SYSTEM AND METHOD FOR SIMULATING DRIVING WHILE BEING COGNITIVELY IMPAIRED

(71) Applicant: INNOCORP, LTD., Verona, WI (US)

(72) Inventors: Patrick Collins, Verona, WI (US);
Timothy Jorgensen, Verona, WI (US);
Debra C. Kusmec-Aguilar, Verona, WI (US)

(73) Assignee: INNOCORP, LTD., Verona, WI (US)

( * ) Notice: Subject to any disclaimer, the term of this patent is extended or adjusted under 35 U.S.C. 154(b) by 36 days.

(21) Appl. No.: 18/886,223

(22) Filed: Sep. 16, 2024

(65) Prior Publication Data
US 2025/0009295 A1 Jan. 9, 2025

Related U.S. Application Data

(60) Continuation-in-part of application No. 18/205,034, filed on Jun. 2, 2023, now Pat. No. 12,156,741, and
(Continued)

(51) Int. Cl.
*G08B 21/00* (2006.01)
*A61B 5/00* (2006.01)

(52) U.S. Cl.
CPC ............ *A61B 5/4845* (2013.01); *A61B 5/002* (2013.01); *A61B 5/6803* (2013.01)

(58) Field of Classification Search
CPC ..... A61B 5/4845; A61B 5/002; A61B 5/6803; A61B 5/18; G16H 20/70; G16H 40/63
(Continued)

(56) References Cited

U.S. PATENT DOCUMENTS 4,079,411 A 3/1978 Engelbrecht et al.
5,362,238 A 11/1994 Slavin
(Continued)

FOREIGN PATENT DOCUMENTS

CN 103843362 A 6/2014
CN 103941422 A 7/2014
GB 2364277 A 1/2002

OTHER PUBLICATIONS

Innocorp Ltd., Drug Abuse Preventative Education—Fatal Vision Goggles, https://web.archive.org/web/20130828133122if_http://fatalvision.com/simulation-goggles/fatal-vision-goggles.html#details, 2013, 6 pages.
(Continued)

*Primary Examiner* — Mark S Rushing
(74) *Attorney, Agent, or Firm* — Quarles & Brady LLP; Yakov S. Sidorin

(57) ABSTRACT

Methodology for demonstrating an effect of impairment during driving includes a set of eyewear devices configured to simulate predefined types of cognitive impairment and an activity set structured to provide depictions of roads for driving and associated pre-determined road conditions, the encountering and/or violating of which triggers a real-time feedback provided to the user participating in a driving exercise. The activity set includes a sensor mat underlying the mat with a depiction of roads and equipped with an array of tags activated in cooperation with the sensor scanner that is repositioned by the user along the roads while simulating the driving to provide such feedback. The choice of the exercise (and the corresponding eyewear device) is accompanied by establishing one-to-one correspondence between a particular depiction of roads and a corresponding set of tags of the array via tuning the sensor scanner to recognize only tags from such set of tags.

19 Claims, 5 Drawing Sheets

Related U.S. Application Data a continuation-in-part of application No. 17/362,935, filed on Jun. 29, 2021, now Pat. No. 12,094,357, said application No. 18/205,034 is a continuation of application No. 17/106,540, filed on Nov. 30, 2020, now Pat. No. 11,678,841, said application No. 17/362,935 is a continuation-in-part of application No. 16/421,052, filed on May 23, 2019, now Pat. No. 11,475,794, which is a division of application No. 15/008,117, filed on Jan. 27, 2016, now Pat. No. 10,366,630.

(60) Provisional application No. 62/108,804, filed on Jan. 28, 2015.

(58) Field of Classification Search
USPC ....................................................... 340/573.1
See application file for complete search history.

(56) References Cited

U.S. PATENT DOCUMENTS

| | | | |
|---|---|---|---|
| 6,145,983 | A | 11/2000 | Schiffer |
| 6,206,521 | B1 | 3/2001 | Kindschuh |
| 7,232,219 | B2 | 6/2007 | Aguilar et al. |
| 8,568,256 | B1 * | 10/2013 | Richardson ............ A63B 43/04 |
| | | | 473/451 |
| 8,764,588 | B2 | 7/2014 | Gill |
| 9,446,856 | B1 * | 9/2016 | Roling ................... G06Q 10/20 |
| 2004/0202812 | A1 | 10/2004 | Congard et al. |
| 2005/0036110 | A1 | 2/2005 | Aguilar et al. |
| 2010/0259716 | A1 * | 10/2010 | Kusmec-Aguilar ... G02C 7/105 |
| | | | 351/47 |
| 2011/0018719 | A1 | 1/2011 | Huang et al. |
| 2013/0040767 | A1 | 2/2013 | Gill |
| 2015/0194067 | A1 | 7/2015 | Kindschuh |
| 2018/0284100 | A1 * | 10/2018 | Agu ..................... A61B 5/4845 |
| 2019/0146219 | A1 * | 5/2019 | Rodriguez, II ....... G06F 3/0482 |
| | | | 345/633 |
| 2019/0287420 | A1 | 9/2019 | Kusmec-Aguilar et al. |
| 2020/0111259 | A1 * | 4/2020 | Sears ................. G02B 27/0172 |

OTHER PUBLICATIONS

Innocorp Ltd., Demonstration: Fatal Vision Marijuana Simulation Experience Maze Activity, https://www.youtube.com/watch?v=yzfrC10McOU, 2016, 13 pages.

Koehler, L., New Goggles Address Effects of Marijuana Use on Drivers, http://fatalvision.com/news-events/2015/new-goggles-address-effects-of-marijuana-use-on-drivers/, Jan. 27, 2015, 4 pages.

Merriam-Webster Online Dictionary, Definition of "maze", https://www.merriam-webster.com/dictionary/maze, 2022, 1 page.

PCT International Search Report and Written Opinion, PCT/US2016/015152, Apr. 1, 2016, 10 pages.

\* cited by examiner

SYSTEM AND METHOD FOR SIMULATING DRIVING WHILE BEING COGNITIVELY IMPAIRED

CROSS-REFERENCE TO RELATED APPLICATIONS

This US Patent Application is a continuation-in-part from the U.S. patent application Ser. No. 18/205,034 filed on Jun. 2, 2023 and now published as US 2023/0301589, which is a continuation from the U.S. patent application Ser. No. 17/106,540 filed on Nov. 30, 2020 and now granted as U.S. patent Ser. No. 11/678,841.

This US Patent Application is also a continuation-in-part from the U.S. patent application Ser. No. 17/362,935 filed on Jun. 29, 2021 and now published as US 2021/0327301, which is a continuation-in-part from the U.S. patent application Ser. No. 16/421,052, filed on May 23, 2019 and now granted as U.S. Pat. No. 11,475,794, which is a divisional from the U.S. patent application Ser. No. 15/008,117 filed Jan. 27, 2016 and now granted as U.S. Pat. No. 10,366,630, which in turn claims benefit of and priority from the U.S. Provisional Application No. 62/108,804 filed on Jan. 28, 2015.

The disclosure of each of the above-identified patent applications is incorporated herein by reference in its entirety.

TECHNICAL FIELD

The present invention relates to a system and method configured to simulate the effect of impairment of cognitive functions and, more particularly, to a system and method configured to simulate the effects of the recreational use of marijuana and/or consumption of a second drug that either amplifies the impairment effect produced by marijuana or impairs the user on its own during such a routine activity as driving.

RELATED ART

Opioids are highly addictive compounds which cause a spectrum of impairments in users. The United States has had an epidemic of opioid abuse for a number of years which worsened during the COVID-19 pandemic. One tool to reduce usage of and addiction to opioids is to teach the population about the impairments caused while using such compounds. While some teaching tools are known, none of the existing tools adequately provides a first-person experience which provides a user a feeling of the detrimental effects of opioid impairment.

Cannabis is known to produce psychoactive and physiological effects when consumed. Aside from the most common short-term physical and neurological effects (among which there are increased heart rate, increased appetite and consumption of food, lowered blood pressure) and the immediate effects desired by a consumer (such as relaxation, mild euphoria, subjective changes in mood, the "high" or "stoned" feeling), the immediate undesired side-effects include alteration of visual perception, impairment of short-term and working memory, psychomotor coordination and concentration, decrease in short-term memory, dry mouth, impaired motor skills and reddening of the eyes.

Recreational use of marijuana/THC (dried flowers and subtending leaves and stems of the female Cannabis plant) has been shown to impair cognitive functions on a number of levels—from basic motor coordination to more complex executive function tasks, such as the ability to plan, organize, solve problems, make decisions, remember, and control emotions and behavior. The effect produced by using an embodiment of the invention is to give the user an experience of cognitive impairment associated with the recreational marijuana use and demonstrate the susceptibility of the user to this impairment and the degree of potential consequences that may occur, in one instance—the cognitive effects on motor skills.

While THC use affects perception, short-term memory, problem-solving skills, and reaction time, alcohol affects gross motor coordination, judgment, concentration, visual acuity, and reaction time. The combination results in increase of impairment of coordination and increased distortion of the brain's ability to process cognitive information. These impairments negatively impact an individual's driving skills and ability to react appropriately to object and hazards while driving. Some notable impacts from the combination may be: THC inhibits the body's need to vomit. The body's reflex to vomit toxins can save a person's life in a binge-drinking/alcohol poisoning situation. However, when a person also consumes THC, it can inhibit the body's protective response of expelling excess toxins.

Detrimental effects of consuming either of these drugs is especially pronounced while driving.

SUMMARY OF THE INVENTION

Embodiments of the invention provide a system for simulating driving while being cognitively impaired. Such system includes a set of system components, multiple stimulus substrates, a sensor substrate, and a sensor scanning device. The set of system components includes an eyewear device that contains a first optical filter element configured as a lens of the eyewear device. Such first optical filter element has an optical filtering function with a spectral pass-band around a first wavelength (the first wavelength defining a first color) or an overlay affixed to at least a portions of the first optical filter element. When the overlay is present, the overlay includes an overlay pattern that at least partially obscured a peripheral region of the first optical filter element and/or the first optical filter element may include a plurality of independently-controllable regions configured to be switched, when controlled by a processor, to have different levels of opacity. Each of the multiple stimulus substrates bears a respective graphic representation of a respective system of at least partially intersecting roads and road features on the at least partially intersecting roads, a first graphic representation of a first of the multiple stimulus substrates being different from a second graphic representation of a second of the multiple stimulus substrates. The sensor substrate carries thereon an array of programmable radio-frequency identification sensors that are reversibly activatable, and reversibly repositionable across and/or removable from the sensor substrate. The sensor scanner device contains (i) a transmitter and a reader, (ii) a feedback system configured to generate at least one of an audible signal, a haptic signal, and a visually-perceivable signal to be recognized by the user in response to operation of the transmitter and the reader and to generate an electrical signal temporarily interrupting a communication between the transmitter and a sensor of the array in response to activation of the feedback system by the user during a user activity, and (iii) a sensor scanner device support carrying the sensor scanner device configured to operate in sliding contact or rolling contact with the first substrate overlaying the second substrate during the user activity.

Embodiments of the invention additionally provide a method for compiling and using an embodiment of the system of the invention. In one implementation, the method for demonstrating a cognitive impairment of a user during a driving exercise includes a step of providing a component of the set of components of an embodiment of the system identified above to assemble such system; and a step of enabling a sensor scanner device of the system to generate the at least one of an audible signal, a haptic signal, and a visually-perceivable signal to be recognized by the user in response to operation of the transmitter and the reader of the sensor scanner device. In addition, the method may include a step of referencing or tuning the sensor scanner device with respect to a chosen subset of the array the sensors on the sensor substrate to activate the feedback system to generate the at least one of an audible signal, a haptic signal, and a visually-perceivable signal only when the transmitter and a sensor of the subset operably communicate and to de-activate the feedback system when the transmitter and a sensor not belonging to said subset operably communicate. Alternatively or in addition, the method may include a step of overlaying a stimulus substrate corresponding to a chosen subset of the array of sensors over the sensor substrate to have reference indicia of the stimulus substrate spatially overlap respectively-corresponding reference indicia of the sensor substrate to position the sensors of the chosen subset substantially under pre-identified road features depicted in the graphic representation at the stimulus substrate; and a step of repositioning a sensor scanner device in sliding or rolling contact with the stimulus substrate along a depiction of a road of the system of at least partially intersecting roads.

Embodiments also provide a computer program product containing tangible non-transitory memory storage that contains program code(s) thereon configured to carry out steps of a method of the invention when loaded on a computer processor.

BRIEF DESCRIPTION OF THE DRAWINGS

The invention will be more fully understood by referring to the following Detailed Description of Specific Embodiments in conjunction with the Drawings, of which.

Figure 1:
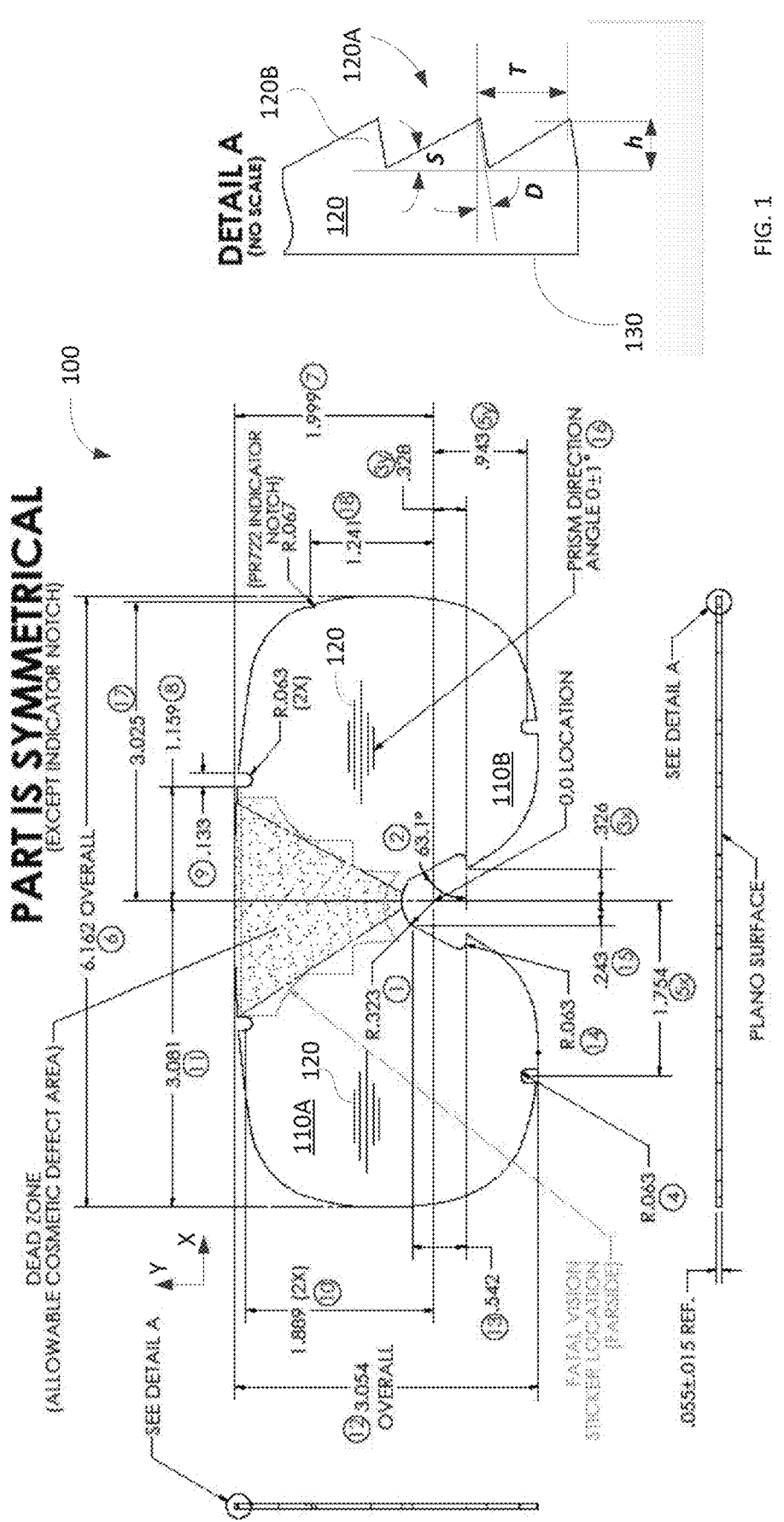
FIG. 1 illustrates an embodiment of an eyewear device configured to simulate the sensation of impairment caused by consumption of marijuana.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. While specific embodiments are depicted in the figures with the understanding that the disclosure is intended to be illustrative, these specific embodiments are not intended to limit the scope of invention the implementations of which are described and illustrated herein.

DETAILED DESCRIPTION OF THE INVENTION

A problem of practical simulation of cognitive impairment caused by marijuana and/or a secondary common drug taken simultaneously and/or opioid has been partially addressed in, for example, U.S. patent application Ser. No. 18/205,034 (referred to herein as the '034 application) and/or Ser. No. 17/362,935 (referred to herein as the '935 application). In these applications, methodologies have been considered of exposing a user to perceiving the ambient environment through a judiciously structured system of optical filters (which may interchangeably be referred to as goggles or eyewear device) configured to distort the vision of the user within the pre-determined field of view (FOV) such as to either i) deviate a line of sight of the user in comparison with the default line of sight existing in absence of the eyewear device and/or ii) remove at least one color, as perceived by the user looking at the ambient environment through the eyewear device from the color gamut that characterizes the ambient (in the case of the marijuana-caused impairment) or obscure/block at least a portion of the field of view (in case of the opioid-caused impairment). The purpose of exercises, performed by the user subject to such limited and/or distorted perception of reality, was to provide feedback—generated by an independent observer—that would in measured, assessed practical terms indicate the degree of severity of the simulated impairment. The discussed modalities were limited, however, in that a real-time demonstration of the cognitive impairment—which is particularly important under conditions of driving on the road—was not addressed. Implementations of the present invention address this shortcoming by devising a reconfigurable system, method, and kit for providing substantially immediate feedback demonstrating an effect of such cognitive impairment to a participant performing a driving exercise. For the purposes of this disclosure and accompanying claims, a real-time performance of a system is understood as performance which is subject to operational deadlines from a given event to a system's response to that event. For example, a real-time extraction of information (such as a spatial location) from a buffer of a computerized device may be one triggered by the user and executed simultaneously with and without interruption of such device during which this location has been encountered. In particular, the implementation of an exercise of "driving under the influence of marijuana and/or alcohol" may employ, in part, a passive mat or map that carries a graphical representation of a system of the roads—with an option that some of such roads are indicated in color(s) that are not perceivable through the eyewear device, while the external observer counts/marks all errors made by the user/driver under conditions of the simulated impairment (see, for example, FIGS. 1 and 12 of the '935 patent application). Example(s) of the hardware configured to simulate cognitive impairment caused by opioid consumption is presented in the '034 application (see, for example, FIGS. 1, 3, 4 therein).

In practice, only the exclusion of a person providing the driving test/exercise for the user and assessing the results of such test/exercise and substituting such test assessor with real-time human-independent feedback removes inadvertent subjective errors from the earlier methodologies.

To this end, an embodiment of a system of the invention includes not only an eyewear device structured as discussed in reference to FIGS. 1 and 10 of the '935 application and an eyewear device discussed in the '034 application and a car-like-contraption including a steering wheel connected to a roller through a rod (discussed in reference to FIG. 13 of the '935 application), but a combination of a set of passive mats (each carrying a graphic representation of a corresponding system of roads) and a single active mat that is reversibly tunable—as required to establish a one-to-one correspondence with a given of the passive mats—for operating with and recognizing only a set of roads depicted on such given passive mat. In particular, each of the set of passive mats (referred to herein as stimulus substrates) contains a depiction of a corresponding network of roads configured to be used with a particular type of an eyewear device, while the single active mat or substrate (referred to herein as a sensor substrate) is reconfigurable for use with each and every of the stimulus substrates.

As the skilled artisan will appreciate from the discussion below, the spatial reconfiguration of the sensor substrate is required for operation of an embodiment of the invention and is performed with the use of a set of identification sensors that are configured to be repositionable at and/or removable from the sensor substrate. Similarly, the process of operational tuning of the sensor substrate, which is required for using the sensor substrate use only with a chosen stimulus substrate in a chosen driving exercise (and not with another stimulus substrate from the set) is performed with the use of an operational sensor that is associated with the chosen stimulus substrate.

Components of an embodiment of the system configured for demonstration of effects of cognitive impairment during driving are now discussed below.

To this end, FIG. 1 schematically illustrates one of related embodiments of the eyewear 100 (or eyewear device, or goggles—which terms may be used interchangeably) configured for causing a sensation of impairment similar to that produced by intake of marijuana and a combination of marijuana and alcohol, respectively (for more details, the reader is referred to the '935 application). At least one of the lenses 110A, 110B includes a spectral optical filter having a pass-band characterized by a central wavelength. The spectral characteristic of the lenses 110A, 110B is substantially the same across the lenses within their bounds. The lenses can be made of glass or a flexible plastic sheet. In the latter example, the typical thickness of the lenses is about 0.05 inches. Due to the parameters of the spectral transmission, the lenses are perceived by the user as optically transparent elements the color of which is substantially the same at any point within the bounds of the lenses. It is notable that, according to the idea of the invention, both the spectral pass-band of a spectral filter of the embodiment and the central wavelength of such pass-band are judiciously defined in operational correspondence with the spectral characteristics of at least one of the two radiant objects of the embodiment.

In addition to pre-determined spectral pass-band of the filters 110A, 110B of FIG. 1 and filters 1010A, 1010B of FIG. 19, each of the filters may optionally contain an additional spatial pattern at a body of such optical filter. The spatial pattern is judiciously configured to define different phase delays for two different light beams that propagate through the optical filter at different points. Referring again to FIG. 1, for example, a non-limiting example of such pattern is shown in inset as a prismatic surface-relief structure 120 defined at the surface of each of the filters 110A, 110B by rulings 120A (which may be spatially periodic or non-periodic, depending on the details of particular implementation). As shown, the prismatic structure is periodic and includes linear rulings/grooves separated by the prismatic elements 120B that extend, substantially, across the whole clear aperture of the filters 110A, 110B. While the direction in which the prismatic structures 120B (and the rulings 120A) are extended preferably substantially coincides with a horizontal direction as defined by the use of the goggles 100 (and shown as the x-axis in FIG. 1), it is appreciated that a related embodiment with certain angular deviation between the direction of the rulings 120A and the x-axis, possible in practice, is still within the scope of the invention. An example of such deviation is indicated in FIG. 1 as +/−1 degree, but in practice can be several degrees, for example +/−5 degrees or even within the range of +/−10 degrees.

The spatial pattern 120 of the optical filters 110A, 110B in the specific example of FIG. 1 is defined by the period T, the slope angle S (an angle between a facet of an element of the prismatic structure with respect to the planar surface 130 of the optical filter 110A, 110B), the draft angle D, and the height h. It may be preferred that the period T of the pattern is chosen such as to not produce any visually perceivable optical effects (such as the optical diffraction effect) when viewed by the user. At the same time, the period T should be such as to be not easily discernible. Accordingly, in one embodiment the value of T could exceed the wavelength of visible light while being smaller than, for example, a millimeter. Additional technical details of the embodiment 100 are provided in the '935 patent application.

In a related non-limiting embodiment of the eyewear device 100 the spatial pattern 120 may be judiciously oriented at an angle (in one specific case—at a substantially 45-degree angle) with respect to the horizontal direction (denoted by the local x-axis) to stimulate the impairment caused by simultaneous consumption of marijuana and a second drug that amplifies the impairment effect produced by marijuana. This and other structural and/or operational details of related but not-limiting variations of the embodiment 100 are discussed in more detail in the '935 application, and are not addressed here for simplicity of presentation. Overall, it is appreciated that the embodiment 100 includes an optical filter having an optical filtering function defining a spectral pass-band around a first wavelength, the first wavelength defining a first color and, optionally, having a spatial pattern defining different phase delays for first and second collimated light beams that are incident substantially normally at the optical filter element.

Figure 2:
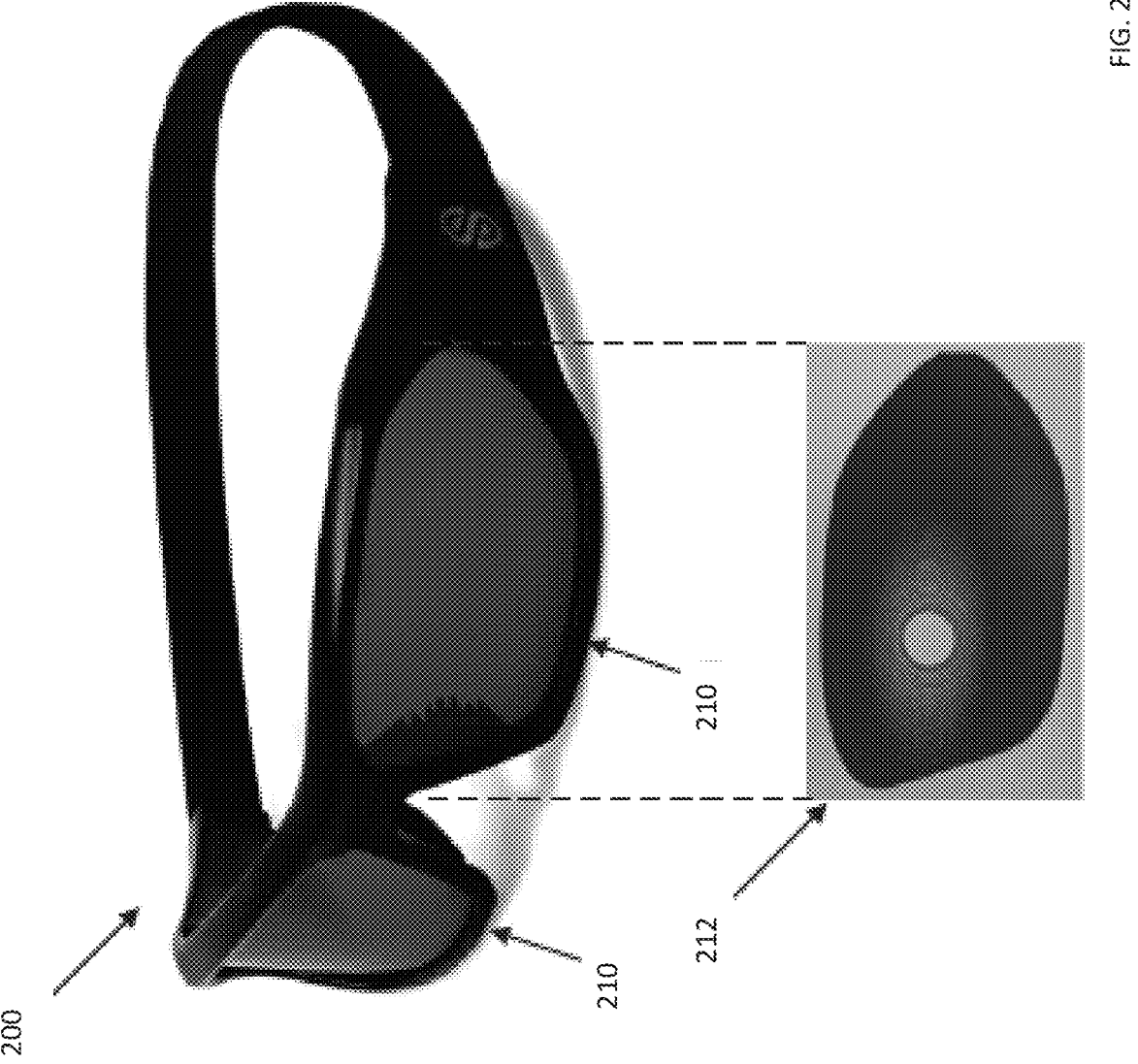
FIG. 2 shows an embodiment of an eyewear device (top) and an overlay (bottom) configured to simulate the sensation of impairment caused by opioid intake.

FIG. 2 shows an embodiment of an eyewear device 200 (top) configured to stimulate an impairment cause by opioid consumption and an associated overlay (bottom), as discussed in more detail in the '034 application. According to the idea of the invention, the eyewear device 200 includes one or more optical filter elements 210 (interchangeably referred to as lenses) having spatial regions that may be controlled to partially or completely obscure all or part of the viewing area as well as corresponding overlay(s) 212 that may be affixed to at least a portion of the corresponding optical filter element to partially or completely obscure certain portions of the user's visual field. The overlay 212 is structured to include a pattern that at least partially obscures a region of the at least one optical filter element 210 when the overlay is attached to it. In the bottom portion of FIG. 2 the dashed lines are used to indicate indicating that the overlay 212 would be placed onto the optical filter element 210. (When the eyewear 200 includes two optical filter elements each of which is configured as a corresponding lens of the eyewear, as shown in the non-limiting example of FIG. 2, another overlay that is a mirror image of the first overlay would be placed onto the other lens 210.) In certain embodiments, the optical filter element 210 may include (e.g. may be subdivided into) a plurality of independently-controllable (for example, with the use of a computer processor operably connected with the filter element) regions that are configured to be operably switched to assume different levels of opacity and/or to be activated and deactivated in various patterns in sequences that produce effects helping the user experience and gain understanding of some of the impacts of opioid consumption (such as divided attention failure and nodding out, for example). This and other structural and/or operational details of related but not-limiting variations of the embodiment 200 are discussed in more detail in the '034 application, and are not addressed here for simplicity of presentation. In at least one embodiment, an eyewear device 200 may be equipped with a dedicated controller such as a processor, memory storage, a power supply (e.g. a battery such as a rechargeable battery), and a communication system (e.g. a wireless communication modality such as Bluetooth or a suitable wired communication mechanism).

Overall, a skilled artisan now readily appreciates that the embodiment 200 (or a related embodiment) includes an optical filter element that includes at least one (and, preferably, a plurality of) independently-controllable regions configured to be switched (when controlled by a processor) to have different levels of opacity. The optical filter element also includes an overlay that is affixed to at least a portion of the first optical filter element, which overlay pattern is structured to at least partially obscure a peripheral region of the optical filter element.

Furthermore, it is appreciated that a related embodiment of the eyewear device may be structured to combine the features of the embodiment 100 (or a related embodiment) with the features of the embodiment 200 (it a related embodiment) in that the optical filter of the related embodiment may be structured to possess both the (optical filtering function and/or the spatial pattern) of the embodiment 100 and the (at least one independently-controllable region and/or the overlay) of the embodiment 200.

Figure 3B:
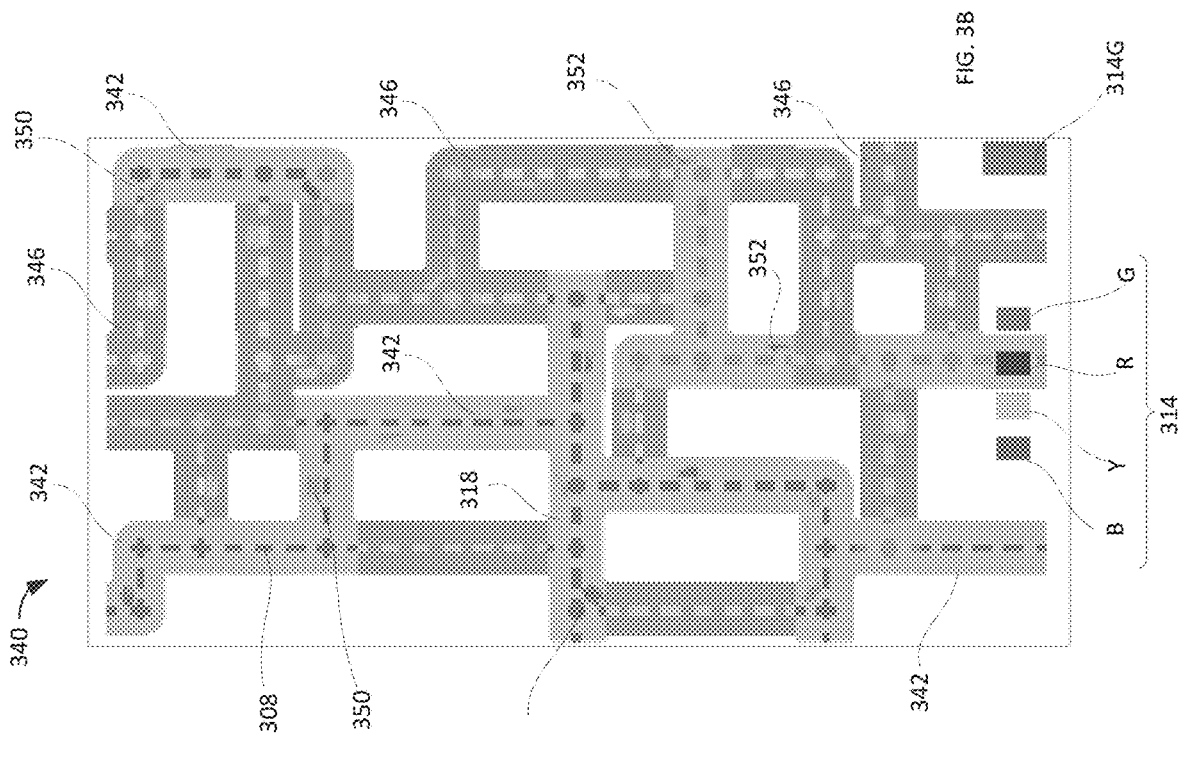
FIGS. 3A and 3B provide examples of embodiments of a stimulus substrate or mat.
Figure 3A:
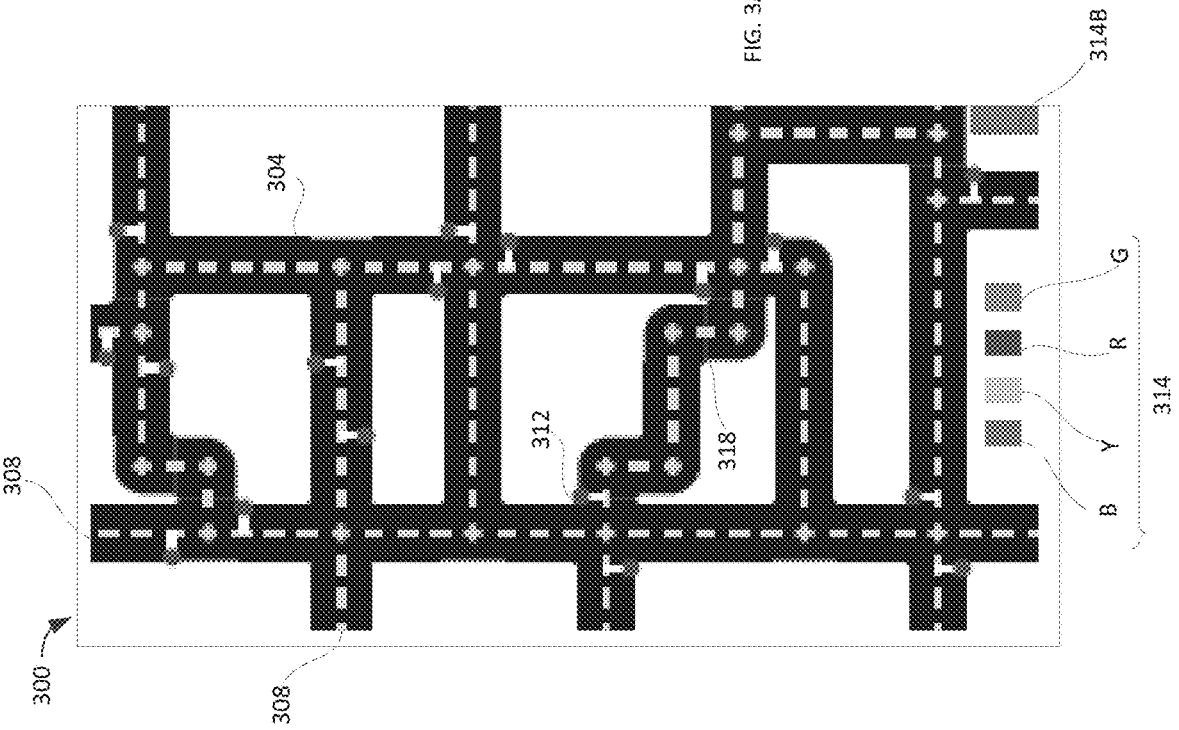
Figure 4:
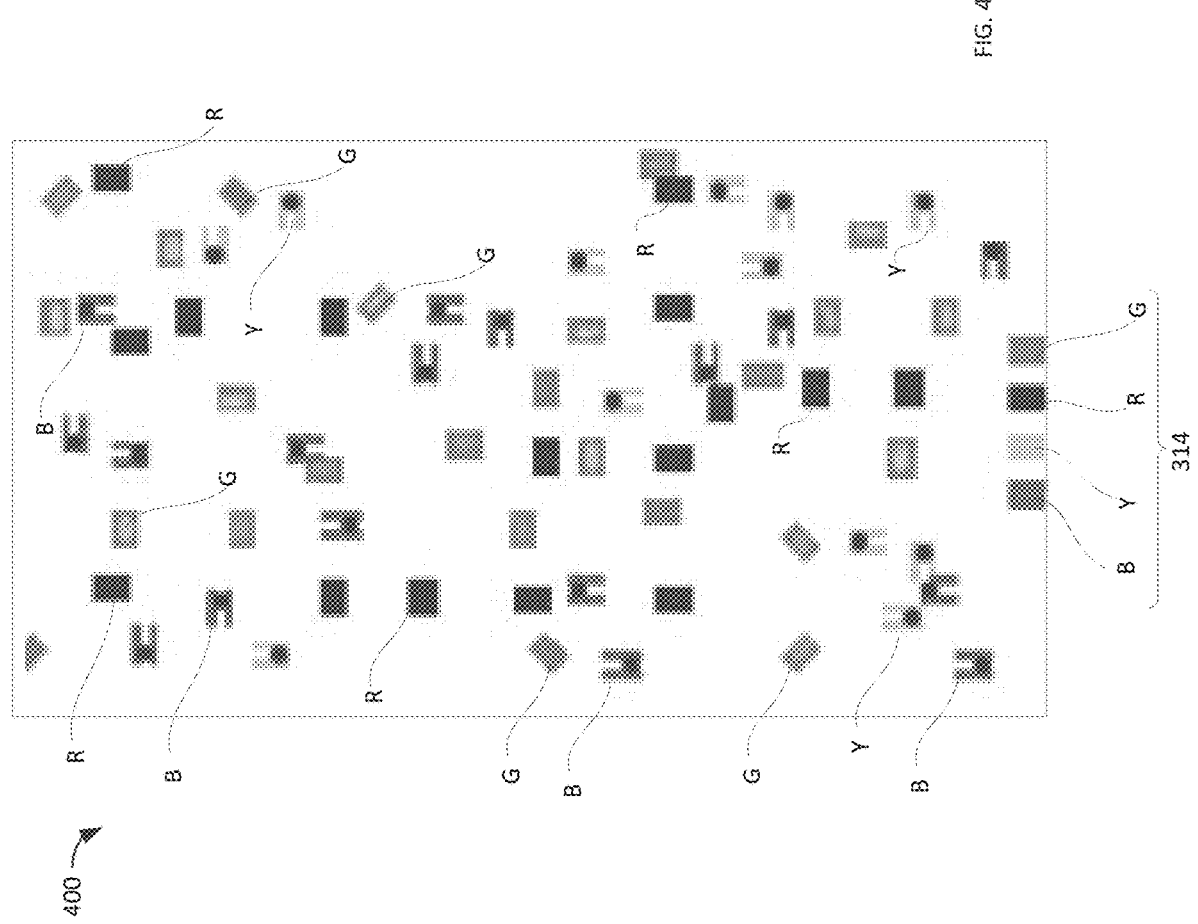
FIG. 4 illustrates an example of a sensor substrate of an embodiment of the invention.

As was alluded to above, according to the idea of the invention, driving exercises configured to demonstrate the cognitive impairment of the user/driver utilizes—in addition to an embodiment of the eyewear device to be worn by the user—a combination of a set of stimulus mats or substrates and a sensor mat or substrate, which aggregately provide the opportunity for the user to choose a driving path and to experience various road conditions and limitations. The purpose of a given driving exercise is for the wearer of an embodiment of the eyewear device (who is, as a result, impaired in terms of how he/she perceives the space available for being observed through the eyewear device) to complete a particular portion of 'travel along the system of roads' depicted on the stimulus substrate with as few as possible driving violations (the violations in this case will be caused—if not recognized through the eyewear device—by the road conditions depicted on stimulus substrate). The feedback to the 'user/driver' is provided, in real time, with the use of a processor-governed feedback apparatus (or a sensor scanner device, judiciously configured to sense those of the sensors distributed across the sensor substrate that correspond to the stimulus substrate chosen for this given driving exercise and to react only to sensing these specific sensors (regardless of whether other of the sensors are being recognized by the sensor scanner device). These guidelines identify particular technical features of the constituent parts of a system of the invention. FIGS. 3A, 3B, 3C discussed below illustrate examples of different stimulus substrates (each carrying a respective graphic representation of a corresponding set or network of at least partially intersecting roads dedicated to a particular driving activity), while FIG. 4 schematically depicts an embodiment of the sensor substrate. The "driving" along a road depicted on a given stimulus substrate is carried out with the use of a sensor scanner device while the stimulus substrate is placed over the sensor substrate, and with the use of a sensor scanner device that either in physical contact with the stimulus substrate or separated from it by a distance that does not impede the sensing (detection) of the sensors distributed across the sensor substrate with the sensor scanner device.

Embodiment of a Stimulus Substrate

A stimulus mat or substrate is a placemat for a user activity including a driving exercise and employing an RF-based identification of the depicted road conditions. The stimulus substrate contains graphics that denote obstacles that, when perceived and/or scanned over, may or may not cause a feedback signal at the sensor scanner device (discussed below) in response to sensing a given sensor of the sensor substrate (discussed below). The stimulus substrate does not contain sensors. The stimulus substrate guides a user's movement and the use of the sensor scanner device. A stimulus substrate may be substantially of any size and may be used independently of the sensor substrate and sensor scanner device if the user does not want to experience a feedback signal provided by the scanner device (such as an audible, visible, or haptic signal). Preferably, however, the stimulus substrate and the sensor substrate are of substantially equal dimensions. A given stimulus substrate can be swapped out for other stimulus substrate that details a different activity while using the same senso substrate.

Using the depiction of the stimulus substrate 300 of FIG. 3A as an example, the skilled artisan readily recognizes that the system of roads 304 (at least some of which roads may have various road conditions indicia such as that of a median 308, a stop sign 312, a pedestrian crossing 318—particularly, at an intersection of the roads, or other indicia indicating various road conditions such as an area of work on the road, not shown here). In relation to a set up of the sensor substrate (which is discussed below), the repositionable sensors of the sensor substrate are configured to spatially correspond to these road conditions indicia or representations of the corresponding stimulus substrate. The graphical representations carried by each of the stimulus substrates is judiciously dimensioned across the substrate to correspond and signify a particular driving exercise, and is marked as such (here, in the corner of the substrate 300) with a corresponding tuning graphic or label 314B. (The multiplicity of sensor labels—here shown as a group 314 including labels B, Y, R, G—that designates all available driving exercises, four exercises B, Y, R, and G in the specific illustrated case.) The marker provided by the tuning label such as 314B serves as an identifier of the one-to-one correspondence between a given stimulus substrate (in this case—300) and the specific driving exercise (in this case—exercise B) and, at the same time, is used for tuning of the system to activate the system with respect to this particular exercise to be able to recognize and respond to the indicia of the road conditions identified only in this particular stimulus substrate (as discussed below in detail).

Depending on the specifics of a particular driving exercise to which the embodiment of the invention is tuned, at least a portion of the graphic representation carried by a given stimulus substrate may be configured to reflect light at a wavelength of wavelengths that represent color(s) complementary to color(s) represented by a pass-band of the optical filtering function of an embodiment of the eyewear used during such particular driving exercise. This situation is illustrated in FIG. 3B, showing an embodiment 340 of another stimulus substrate (of the set of stimulus substrates that is part of the overall system) in which some of the depicted roads or portions of the roads 342 are indicated in one color discernable by the wearer of the eyewear device 100, while some other of the depicted roads or portions of the roads 346 are presented in a different color, not necessarily easily discernable by the wearer of the eyewear device 100. The network of the roads depicted on the stimulus substrates 340 additionally contains indicia of various road conditions, among which there may be a depiction of a car 350 on the road, a person 352 jay-walking or using the pedestrian crossing, a blockage 354 of the road, to name just a few. Depending on the specifics of a particular implementation of the substrate 340, these road conditions may be indicated in a color that is not well discernable by a wearer of the eyewear device on the background of the color of the particular road, or otherwise. The embodiment 340 is shown to be marked with the tuning graphic or label 314G, thereby indicating that it lends itself to being used in the driving exercise G (from the available in this example exercises B, Y, R, and G) and that for such exercise, this substrate 340 should be paired with a corresponding embodiment of the eyewear device.

The skilled artisan now appreciates that an embodiment of the system of the invention generally includes multiple stimulus substrates each bearing a respective graphic representation of a respective system of at least partially intersecting roads and road features or conditions on such roads. The graphic representation carried by one of the multiple stimulus substrates is generally different from the graphic representation carried by another of the multiple stimulus substrates.

To allow the user to engage in a chosen driving exercise, the corresponding stimulus substrate is paired with (in practice—laid over) a sensor substrate the dimensions of which are substantially equal to those of the stimulus substrate.

Embodiment of the Sensor Substrate

The sensor substrate contains an array of programmed sensors or tag configured to make use of RF-identification technology. In operation, the sensor substrate is associated with (equipped with) multiple RFID sensors or tags containing several groups of sensors configured such that a given group is used in a given driving exercise. Each set of sensors is placed and programmed in a specific pattern that corresponds to unique use cases.

In reference to FIG. 4, and using the example of four different driving exercises identified as B, Y, R, and G (see FIGS. 3A, 3B), the embodiment 400 of the sensor substrate carries thereon an array of sensors or tags including multiple groups of sensors, each group (here, the group of sensors B, the group of sensors Y, the groups of sensors R, and the groups of sensors G) including sensors of only one type (B, Y, R, and G, respectively) that have RFID operational characteristics different from those of the sensors of another type. The sensors are reversibly and removably affixed to the sensor substrate at locations that—should a corresponding stimulus substrate be overlapped with the sensor substrate—would directly correspond to and present to the locations of road conditions indicated at the corresponding stimulus substrate. For example, the sensors B (to be used during the driving exercise B) are placed on the sensor substrate at positions directly corresponding to the positions at which indicia of road conditions are present across the stimulus substrate configured to be used during the driving exercise B. Overall, the array of sensors generally includes multiple sensors of each of multiple sensor types, with sensors of a first type operably correspond to a first stimulus substrate of the multiple stimulus substrates and sensors of a second sensor type operably correspond to a second stimulus substrate of the multiple stimulus substrates,

Embodiment of the Sensor Scanner Device

Figure 5:
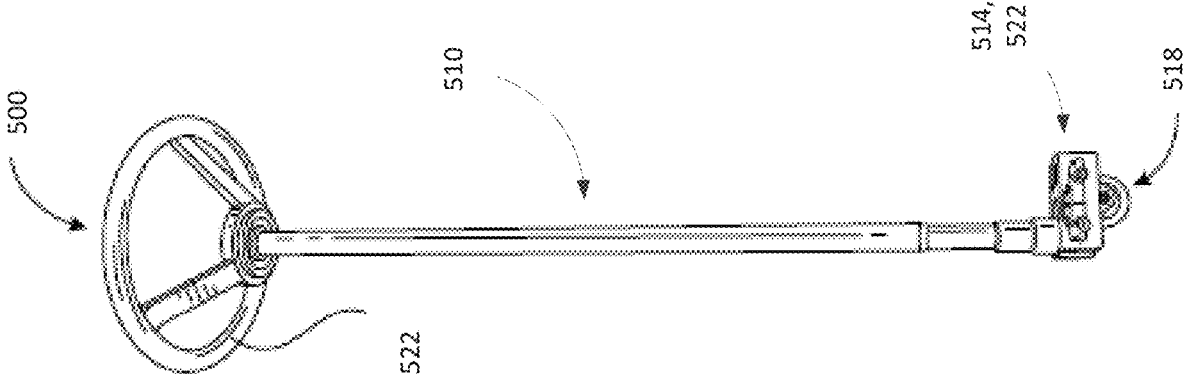
FIG. 5 depicts an embodiment of a sensor scanner device.

When implemented according to the idea of the invention, the sensor scanner device (or, sensor scanner, for short) is a device that provides user-perceivable feedback (in a form of a haptic signal, an audible signal, and/or a visually-perceivable signal, for example) to the user when used in conjunction with the sensor substrate overlaid with a particular stimulus substrate. One specific non-limiting implementation 500 of the sensor scanner device is schematically shown in FIG. 5. The device 500 includes a sensor scanner device support (shown as a body 510 dimensioned in this example as a rod—optionally, with telescopically adjusted length to accommodate the users of different heights—with the housing or holder 514 at a distal end of the body 510) that is configured to operate in sliding contact or rolling contact (as shown—with the use of a wheel/roller 518) with the stimulus substrate overlaying the second sensor substrate during the user activity. In one implementation the sensor scanner device may be configured to resemble a car-like-contraption that includes a steering wheel or handle 522 connected to a roller 518 through the rod.

The device 500 is structured to include electronic circuitry configured as a transmitter, electronic circuitry configured as a receiver and reader of signals produced by the sensors or tags of the sensor substrate, and electronic circuitry configured as a feedback system, aggregately marked with a numeral 526. At least some of the involved electronic circuitry can be enclosed within or attached to the rod and/or, optionally, housed within the housing 514. In one embodiment, the feedback system is configured to generate at least one of an audible signal, a haptic signal, and a visually-perceivable signal to be recognized by the user in response to operation of the transmitter and the reader and to generate an electrical signal temporarily interrupting a communication between the transmitter and a sensor of said array in response to activation of the feedback system by the user during a user activity. The electronic circuitry 526 may include or be complemented with a timer and a processor (in operable communication with the transmitter, the reader, and the feedback system) as well as a tangible non-transitory memory storage operably connected to such processor (the memory storage may contain a set of instructions which, when executed by the processor, cause the processor to operate a timer to record an amount of elapsed time while a user performs the user activity and/or to reversibly activate the transmitter and/or the reader and/or the feedback system.

Example of Practical Use of an Embodiment of the System

Figure 6:
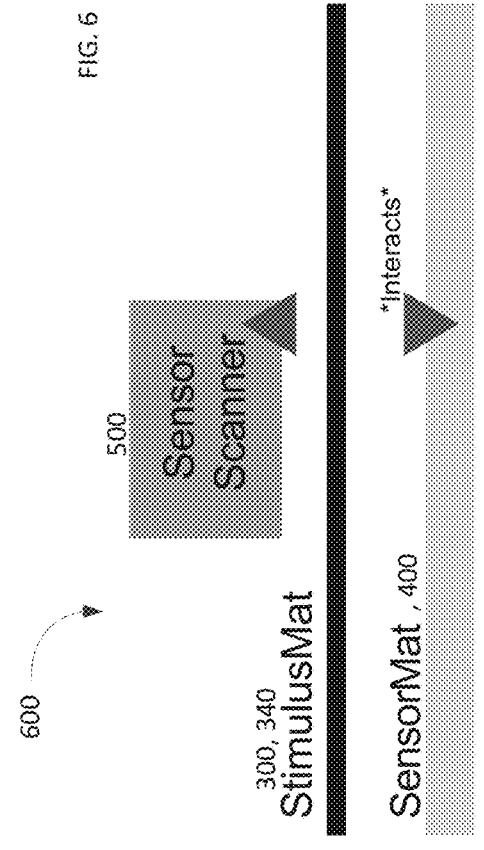
FIG. 6 illustrates spatial coordination of components of an embodiment of the system of the invention during a driving exercise.

The schematic of FIG. 6 illustrates mutual positioning and orientation of some of the components of an embodiment of the system of the invention (which, aggregately, may referred to as a Real-Time Feedback System, or RTFS, configured to provides immediate, real-time feedback on decisions made by the user during a driving exercise. What is shown is the activity set 600 intended to be used in conjunction with an embodiment of the eyewear device during a driving exercise.

In one specific case, the sensor substrate or mat can be fabricated from 13 oz Scrim Banner and printed in full color with identification of locations to place sensors on. The RFID tag or sensor can be configured as a near-field communication NFC) sensor, for example as a a NXP Ntag-213 ISO 14443 Type A, NFC Forum Type 2. These may be inlaid into 50.8×76.2 mm 4-color printed stickers with 3M adhesive stickers. The stimulus substrate or mat may be fabricated from a multiple-color printed close cell bonded neoprene, while the sensor scanner device may employ a NFC Forum Type 2 antenna and reader, an appropriate battery, a custom PCB board, a haptic motor, a buzzer, and an LED.

The purpose of using an embodiment of the RTFS is to enrich education. The related art of providing practical exercised with the use of a system stimulating cognitive impairment of the user relies on a proctor or observer to keep track of the mistakes made by the main participant. Using the RTFS provides immediate feedback to users, highlighting their mistakes and decisions and deepening their learning. This directly ties their actions to outcomes, pairing the stimulus with the response. Additionally, it creates a more realistic experience for those using our driving mats. When "driving" (that is, repositioning the distal end of the sensor scanner device along a depiction of the road of the stimulus substrate laid over the sensor substrate, the user observes the road(s) through the eyewear device and "feels" the road via perceiving a feedback signal generated by the feedback system each time when he/she does not react to a road condition depicted on the stimulus substrate as a result of cognitive impairment induced by the eyewear device. For example, when the user drives across the graphical representation of a crosswalk without stopping, the sensor of the sensor substrate located underneath the depiction of the cross walk and the sensor scanner device interact to produce a feedback signal such as honking or vibration. Practical studies performed with embodiments of the invention demonstrated that feedback provided to the user in real time does, in fact, improve a learner's interest, awareness, and enthusiasm.

In particular, a participant, using the sensor scanner, will run over/drive over graphics when he/she fails to see an obstacle, such as a stop sign or tree branch on the stimulus substrate. A corresponding RFID sensor is below the graphic, on the sensor substrate. If the sensor scanner device is properly tuned, it responds to the participant's running over the obstacle, then tripping the scanner to beep and vibrate, indicating the user has made a mistake. As a result of the tuning of the sensor scanner device, if the user should run over an RFID tag that is placed on the sensor mat but does not have a graphic on the stimulus substrate above, the sensor scanner device reads the tag but not trigger a feedback response: the feedback system of the sensor scanner device is configured to respond to only certain sets of coded information on the tags/sensors it reads and is tuned to. This configuration allows multiple sets of sensors to be installed on a single sensor substrate without causing interferences between their intended activities and respectively corresponding stimulus substrates.

In preparation to the driving exercise, the user places the sensor substrate on the ground, sensors facing up (the bottom of the sensor substrate is appropriately labelled) and place the chosen stimulus substrate over top of the sensor substrate while aligning a bottom edge of the stimulus substrate with that of the underlying sensor substrate to ensure that the stimulus substrate substantially completely covers the sensor substrate. Then, as part of the process of tuning the sensor scanner device and upon the initiation of the scanner device, the use passes the distal end (the roller) of the sensor scanner device over the specific tuning graphic on the stimulus substrate to sense the corresponding RFID tuning sensor located below the tuning graphic on the sensor substrate to produce a "handshake" and mutual operation recognition between the electronics of the sensor scanner device and this particular tuning sensor, as a result of which the sensor scanning device will not react when in the vicinity of any other type of sensor but only that corresponding to the type of the tuning sensor. The tuning process is complete when the feedback system produces a feedback signa in response to the tuning sensor: this denotes that the user has sensed the sensor of the particular type of sensors to which the tuning sensor of the sensor substrate belongs. Optionally, the sensor scanner device can be additionally selectively muted, letting the user silence the feedback signals when the user appropriately perceives obstacles/road conditions on the stimulus substrate (for example, the user recognizes the stop sign, holds the appropriate mute button on the body of the sensor scanner device, and then "drives" past the stop sign). When muted, the sensor scanner device may display a light, signifying to the user and observers that the sensor scanner device has been muted.

In some embodiments, a timer may be provided independently from the circuitry contained in the body of the sensor scanner device, to be used as part of the instructional or educational use of the eyewear device (such as 100 or 200 or a similar eyewear device) and the activity set 600. In the example of using the eyewear device 200, in one particular embodiment the software (e.g. the app) may include a timer which may be integrated with the control of the sequences of activation and deactivation of the various independently-controllable regions of the lens or lenses 210. In other embodiments a timer may be provided separately from the software (e.g. as a separate handheld timer device).

A time may be measured using the timer to determine how long it takes the user to complete the task, such as correctly and without violation of the rules of driving to conclude a trip from one point on the network of the roads depicted on a stimulus substrate to another point while being subject to the simulated cognitive impairment. This time may be compared to a benchmark time which indicates how long the task should take without impairment; in one embodiment the benchmark time may be based on the user's completion of the same task under non-impaired conditions, e.g. without wearing the employed during this particular exercise eyewear device. The user can then see by the difference in the amount of time it takes to complete the task under impaired compared to non-impaired conditions how opioid impairment can make a person's life more difficult. In other embodiments the user may simply try to complete the task within a predetermined time limit, e.g. thirty seconds, 1 minute, 2 minutes, etc., to gain the experience of the difficulty of conducting a relatively easy task such as following a given road path while being subjected to simulated cognitive impairment.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself. The use of these terms in describing a chosen characteristic or concept neither implies nor provides any basis for indefiniteness and for adding a numerical limitation to the specified characteristic or descriptor. Generally, as understood by a skilled artisan, the practical deviation of the exact value or characteristic of such value, element, or property from that stated falls and may vary within a numerical range defined by an experimental measurement error, which error is typical when using a measurement method accepted in the art for such purposes.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

For the purposes of this disclosure and the appended claims, the expression of the type "element A and/or element B" is defined to have the meaning that is equivalent to "at least one of element A and element B".

Implementation of the idea of the invention have been described as including a processor controlled by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While the invention is described through the above-described exemplary embodiments, it will be understood by those of ordinary skill in the art that modifications to, and variations of, the illustrated embodiments may be made without departing from the inventive concepts disclosed herein. Disclosed aspects, or portions of these aspects, may be combined in ways not listed above. Accordingly, the invention should not be viewed as being limited to the disclosed embodiment(s).

The invention claimed is:

1. A system for demonstrating a cognitive impairment of a user, the system comprising:

a set of system components, the set including:

an eyewear device including a first optical filter element configured as a first lens of the eyewear device, the first optical filter element having:

(i) an optical filtering function having a spectral pass-band around a first wavelength, the first wavelength defining a first color, or (ii) an overlay affixed to at least a portions of the first optical filter element, wherein the overlay includes an overlay pattern that at least partially obscures a peripheral region of the first optical filter element, wherein the first optical filter element comprises a plurality of independently-controllable regions configured to be switched, when controlled by a processor, to have different levels of opacity;

multiple stimulus substrates each bearing a respective graphic representation of a respective system of at least partially intersecting roads and road features on said at least partially intersecting roads, a first graphic representation of a first of the multiple stimulus substrates being different from a second graphic representation of a second of the multiple stimulus substrates;

a sensor substrate carrying thereon an array of programmable radio-frequency identification sensors that are reversibly activatable, and reversibly repositionable across and/or removable from the sensor substrate; and a sensor scanner device containing:

(i) a transmitter and a reader, (ii) a feedback system configured to generate at least one of an audible signal, a haptic signal, and a visually-perceivable signal to be recognized by the user in response to operation of the transmitter and the reader and to generate an electrical signal temporarily interrupting a communication between the transmitter and a sensor of said array of programmable radio-frequency identification sensors in response to activation of the feedback system by the user during a user activity, and (iii) a sensor scanner device support carrying the sensor scanner device configured to operate in sliding contact or rolling contact with the first substrate overlaying the second substrate during the user activity.

2. A system according to claim 1, wherein the array of programmable radio-frequency identification sensors includes multiple sensors of each of multiple sensor types, wherein sensors of a first type of the multiple sensor types operably correspond to a first stimulus substrate of the multiple stimulus substrates and sensors of a second sensor type of the multiple sensor types operably correspond to a second stimulus substrate of the multiple stimulus substrates, wherein sensors of a chosen sensor type of the multiple sensor types are distributed across the sensor substrate such that, when a respectively-corresponding stimulus substrate is overlayed onto the sensor substrate to have reference indicia of the stimulus substrate spatially overlap reference indicia of the sensor substrate, said sensors of the chosen sensor type are positioned substantially under pre-identified road features depicted in the graphic representation at the respectively-corresponding stimulus substrate.

3. A system according to claim 1, wherein the scanner sensor device includes a wheel at a first end of the scanner device support and a handle at a second end of the scanner device support, the wheel being configured to be brought into a rolling contact with a given stimulus substrate, of the multiple stimulus substrates, that overlays the sensor substrate to demonstrate the cognitive impairment during the user activity.

4. A system according to claim 1, further comprising:

a processor in communication with the eyewear device and/or with the transmitter, the reader, and the feedback system, and a tangible non-transitory memory storage operably connected to the processor and having stored thereon a set of instructions which, when executed by the processor, cause the processor at least:

to operate a timer to record an amount of elapsed time while the user performs the user activity;

to reversibly activate the transmitter and/or the reader and/or the feedback system; and, when the first optical filter element includes said overlay, to transmit a plurality of signals to the eyewear device to switch at least one of the plurality of independently-controllable regions of the first optical filter between the different levels of opacity.

5. A system according to claim 4, wherein the set of instructions is configured to further cause the processor to transmit the plurality of signals to switch all of the plurality of independently-controllable regions into an opaque state in a single time interval to simulate the user nodding during the user activity.

6. A system according to claim 1, wherein, when the first optical filter element has said optical filter function, the first optical filter element includes a spatial pattern defining different phase delays for first and second collimated light beams that are incident substantially normally at the first optical filter element and propagate through the first optical filter element; or wherein, when the first optical filter element includes the overlay, the overlay further includes a concentric pattern including a central opening aligned with a junction at which the independently-controllable regions converge.

7. A system according to claim 6, wherein said spatial pattern is defined by (i) a relief structure on a surface of the first optical filter element and/or by a spatially-periodic prismatic structure and/or by (ii) a spatial distribution of a refractive index non-uniformity.

8. A system according to claim 6, wherein the first optical filter element has a thickness that is substantially uniform within bounds of the first optical filter element.

9. A system according to claim 6, wherein the eyewear device has a first axis connecting centers of the first lens and a second lens of the eyewear device and a second axis that is substantially perpendicular to the first axis, and wherein the spatial pattern extends substantially straight along a third axis in the surface of the first optical filter element, the third axis being inclined with respect to the first axis.

10. A system according to claim 1, wherein the user activity includes:

while wearing the eyewear device:

placing the sensor scanner device support in contact with the graphic representation of a chosen stimulus substrate that has been operably tuned to and overlayed with the sensor substrate at an appropriate end thereof, and repositioning said appropriate end in contact with and along a road of the system of multiple roads and activating the feedback system to generate said electrical signal once a road feature has been seen through the eyewear device.

11. A system according to claim 1, wherein the graphic representation includes a graphic representation of a median of at least one of the at least partially intersecting roads, a stop sign, a road intersection, and a pedestrian crossing a road of the at least partially intersecting roads.

12. A system according to claim 1, wherein a portion of the graphic representation is configured to reflect light at a wavelength representing a color that is complementary to a color defined by a wavelength of the spectral pass-band.

13. A method for demonstrating a cognitive impairment of a user, the method comprising:

providing a component of the set of components of the system according to claim 1 to assemble the system; and enabling a sensor scanner device of the system to generate the at least one of the audible signal, the haptic signal, and the visually-perceivable signal to be recognized by the user in response to operation of the transmitter and the reader of the sensor scanner device.

14. A method according to claim 13, further comprising:

referencing or tuning the sensor scanner device with respect to a chosen subset of the array of programmable radio-frequency identification sensors on the sensor substrate to activate the feedback system to generate the at least one of the audible signal, the haptic signal, and the visually-perceivable signal only when the transmitter and a sensor of said chosen subset operably communicate and to de-activate the feedback system when the transmitter and a sensor not belonging to said chosen subset operably communicate.

15. A method according to claim 13, further comprising:

overlaying a stimulus substrate, of the multiple stimulus substrates, that corresponds to a chosen subset of the array of programmable radio-frequency identification sensors over the sensor substrate to have reference indicia of the stimulus substrate spatially overlap respectively-corresponding reference indicia of the sensor substrate to position the sensors of the chosen subset substantially under pre-identified road features depicted in the graphic representation at the stimulus substrate; and repositioning the sensor scanner device in sliding or rolling contact with the stimulus substrate along a depiction of a road of the system of the at least partially intersecting roads.

16. A method according to claim 15, further comprising:

operating a timer to record an amount of elapsed time during the user activity to complete said repositioning from a first predetermined point to a second predetermined point, wherein the first and second predetermined points are separated, along the depiction of the road of the system of the at least partially intersecting roads, by one or more of the pre-defined road features.

17. A method according to claim 15, comprising:

during the repositioning, producing the at least one of the audible signal, the haptic signal, and the visually-perceivable signal with the feedback system to indicate the cognitive impairment each time when the user does not activate the feedback system to generate the electrical signal in response to seeing a pre-defined road feature through the eyewear device, wherein the electrical signal is configured to temporarily interrupt communication between the transmitter and a sensor of the chosen subset of the array of programmable radio-frequency identification sensors.

18. A method according to claim 13, comprising:

transmitting, by a processor in communication with the eyewear device, a plurality of signals to the eyewear device to switch at least one of the plurality of independently-controllable regions of the first optical filter element between different levels of opacity during the user activity.

19. A method according to claim 18, wherein the transmitting includes transmitting the plurality of signals to divide attention of the user during the user activity.

* * * * *